(12) United States Patent
Hashimoto (10) Patent No.: US 6,786,869 B2
(45) Date of Patent: Sep. 7, 2004

(54) ULTRASONIC DIAGNOSTIC APPARATUS

(75) Inventor: Hiroshi Hashimoto, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/696,798

(22) Filed: Oct. 30, 2003

(65) Prior Publication Data

US 2004/0133107 A1 Jul. 8, 2004

(30) Foreign Application Priority Data

Nov. 1, 2002 (JP) ........................................ 2002-319171

(51) Int. Cl.$^7$ ................................................ A61B 8/00
(52) U.S. Cl. ..................................... 600/437; 600/448
(58) Field of Search ................................ 600/437–472; 73/595–633; 367/7, 11, 130, 138; 128/916

(56) References Cited

U.S. PATENT DOCUMENTS

| | | | |
|---|---|---|---|
| 5,459,769 A | 10/1995 | Brown | |
| 5,694,937 A | 12/1997 | Kamiyama | |
| 5,735,281 A | 4/1998 | Rafter et al. | |
| 5,935,069 A | * 8/1999 | Chandler et al. | ........... 600/443 |
| 5,944,666 A | 8/1999 | Hossack et al. | |
| 5,947,904 A | 9/1999 | Hossack et al. | |
| 5,971,928 A | 10/1999 | Dodd et al. | |
| 6,149,597 A | * 11/2000 | Kamiyama | .................. 600/458 |
| 6,236,706 B1 | 5/2001 | Hsieh | |
| 6,245,019 B1 | 6/2001 | Kamiyama | |

FOREIGN PATENT DOCUMENTS

| JP | 11194302 | 1/2001 |
|---|---|---|
| JP | 2000063862 | 9/2001 |

* cited by examiner

Primary Examiner—Ali Imam
(74) Attorney, Agent, or Firm—Carl B. Horton, Esq.; Armstrong Teasdale LLP (57) ABSTRACT

For the purpose of allowing confirmation of time progress during a run of a contrast agent protocol and the like on a display screen, time elapsed after freeze-off and time duration of freeze are displayed in a contrast agent protocol display region. In an elapsed-time-after-injection display region, time elapsed from the time of contrast agent injection is displayed. In a countdown display region, time remaining up to a scheduled time for the next operation to be made by an operator is calculated and displayed.

5 Claims, 7 Drawing Sheets

ULTRASONIC DIAGNOSTIC APPARATUS

CROSS REFERENCE TO RELATED APPLICATIONS

This application claims the benefit of Japanese Application No. 2002-319171 filed Nov. 1, 2002.

BACKGROUND OF THE INVENTION

The present invention relates to an ultrasonic diagnostic apparatus, and more particularly to an ultrasonic diagnostic apparatus that allows confirmation of time progress during a run of a contrast agent protocol or time progress during intermittent imaging on a display screen.

Some ultrasonic diagnostic apparatuses have a stopwatch feature that starts time measurement in response to a start operation by an operator, stops the time measurement in response to a freeze-on command by the operator, and displays time elapsed from the start on a display screen. This feature is generally referred to as a contrast timer.

Thus, if a start operation is made when a contrast agent is injected into a subject to be examined, and a freeze-on operation is then made at an appropriate time, time elapsed from the contrast agent injection to the time at which a freeze ultrasonic image is captured can be confirmed on the display screen by using the stopwatch feature.

Imaging with a contrast agent is set out in Japanese Patent Application Laid Open Nos. 2001-17427 and 2001-252271.

By the stopwatch function in the conventional ultrasonic diagnostic apparatus, how long after contrast agent injection a freeze ultrasonic image was captured can be confined on a display screen or printed image.

However, how long has passed while observing a freeze ultrasonic image, or how long has passed from a freeze-off operation cannot be confirmed on a display screen. Moreover, during intermittent imaging in which a freeze ultrasonic image is automatically updated every one minute, for example, how long has passed after a current ultrasonic image was captured, or how much wait time remains until the ultrasonic image is next updated cannot be confirmed on a display screen.

Accordingly, there has been a problem that to confirm time progress during a run of a contrast agent protocol or time progress during intermittent imaging on a display screen, a watch must be separately provided and checked.

SUMMARY OF THE INVENTION

It is therefore an object of the present invention to provide an ultrasonic diagnostic apparatus that allows confirmation of time progress during a run of a contrast agent protocol or time progress during intermittent imaging on a display screen.

In its first aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; and freeze time duration measuring means for measuring and displaying time duration of the freeze state.

In the ultrasonic diagnostic apparatus of the first aspect, since the time duration of the freeze state is measured and displayed, how long has passed while observing the freeze ultrasonic image can be confirmed on a display screen. Therefore, the operator need not check a separately provided watch, and can concentrate on the display screen to move ahead with a contrast agent protocol.

In its second aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; and freeze-off countdown means for measuring and displaying time remaining to a time at which a next freeze-off operation is to be made.

In the ultrasonic diagnostic apparatus of the second aspect, since the time remaining to a time at which a next freeze-off operation is to be made is measured and displayed during a run of a contrast agent protocol, the operator need not check a separately provided watch, and can concentrate on the display screen to move ahead with the contrast agent protocol.

In its third aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; freeze time duration measuring means for measuring and displaying time duration of the freeze state; freeze-on countdown means for measuring and displaying time remaining to a time at which a next freeze-off operation is to be made; and selection operating means for allowing the operator to select and activate both or one of the freeze time duration measuring means and the freeze-off countdown means.

In the ultrasonic diagnostic apparatus of the third aspect, since the time duration of the freeze state and/or the time remaining to the time at which the next freeze-off operation is to be made can be confirmed on the display screen, the operator need not check a separately provided watch, and can concentrate on the display screen to move ahead with the contrast agent protocol.

In its fourth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; and elapsed-time-from-freeze-off measuring means for measuring and displaying time elapsed from freeze-off.

In the ultrasonic diagnostic apparatus of the fourth aspect, the time elapsed from freeze-off is measured and displayed, how long has passed after turning off freeze can be confirmed on the display screen. Therefore, the operator need not check a separately provided watch, and can concentrate on the display screen to move ahead with the contrast agent protocol.

In its fifth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; and freeze-on countdown means for measuring and displaying time remaining to a time at which a next freeze-on operation is to be made.

In the ultrasonic diagnostic apparatus of the fifth aspect, since the time remaining to the time at which the next freeze-on operation is to be made is measured and displayed during a run of a contrast agent protocol, the operator need not check a separately provided watch, and can concentrate on the display screen to move ahead with the contrast agent protocol.

In its sixth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freeze control means for maintaining a state displaying the last ultrasonic image in response to a freeze-on operation by an operator and resuming production/display of a new ultrasonic image in response to a freeze-off operation by the operator; elapsed-time-from-freeze-off measuring means for measuring and displaying time elapsed from freeze off; freeze-on countdown means for measuring and displaying time remaining to a time at which a next freeze-on operation is to be made; and selection operating means for allowing the operator to select and activate both or one of the elapsed-time-from-freeze-off measuring means and the freeze-on countdown means.

In the ultrasonic diagnostic apparatus of the sixth aspect, since the time elapsed from freeze-off and/or the time remaining to the time at which the next freeze-on operation is to be made can be confirmed on the display screen, the operator need not check a separately provided watch, and can concentrate on the display screen to move ahead with the contrast agent protocol.

In its seventh aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; operation-at-start-of-injection means for operation by the operator at the start of contrast agent injection; and elapsed-time-from-injection measuring means, which is not stopped even if freeze-on is commanded, for measuring and displaying time elapsed from an operation of the operation-at-start-of-injection means.

In the ultrasonic diagnostic apparatus of the seventh aspect, since the time elapsed from contrast agent injection is measured and displayed without stopping even if freeze-on is commanded after the contrast agent injection, how long has passed after the contrast agent was injected can be confirmed on the display screen. Therefore, the operator need not check a separately provided watch, and can concentrate on the display screen to move ahead with the contrast agent protocol.

In its eighth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on operation by an operator; operation-at-start-of-injection means for operation by the operator at the start of contrast agent injection; and injection-freeze countdown means for measuring and displaying time remaining to a time at which a first freeze-on operation is to be made after operation of the operation-at-start-of-injection means.

In the ultrasonic diagnostic apparatus of the eighth aspect, since time remaining to the time at which the first freeze-on operation is to be made after contrast agent injection is measured and displayed during a run of a contrast agent protocol, the operator need not check a separately provided watch, and can concentrate on the display screen to move ahead with the contrast agent protocol.

In its ninth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; operation-at-start-of-injection means for operation by the operator at the start of contrast agent injection; elapsed-time-from-injection measuring means, which is not stopped even if freeze-on is commanded, for measuring and displaying time elapsed from an operation of the operation-at-start-of-injection means; injection-freeze countdown means for measuring and displaying time remaining to a time at which a first freeze-on operation is to be made after operation of the operation-at-start-of-injection means; and selection operating means for allowing the operator to select and activate both or one of the elapsed-time-from-injection measuring means and the injection-freeze countdown means.

In the ultrasonic diagnostic apparatus of the ninth aspect, since the time elapsed from contrast agent injection and/or the time remaining to the time at which a first freeze-on operation is to be made after contrast agent injection is measured and displayed during a run of a contrast agent protocol, the operator need not check a separately provided watch, and can concentrate on the display screen to move ahead with the contrast agent protocol.

In its tenth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; time-measurement-start commanding/operating means for use by the operator to operate to command start of time measurement; and elapsed-time measuring means, which is not stopped even if freeze-on is commanded, for measuring and displaying time elapsed from an operation of the time-measurement-start commanding/operating means.

In the ultrasonic diagnostic apparatus of the tenth aspect, since the time elapsed from start of time measurement that is arbitrarily initiated is measured and displayed without stopping even if freeze is turned on after the start of time measurement, how long has passed from start of examination, for example, can be confirmed on the display screen. Therefore, the operator need not check a separately provided watch, and can concentrate on the display screen to move ahead with the contrast agent protocol.

In its eleventh aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; time-measurement-start commanding/operating means for use by the operator to operate to command start of time measurement; and stopwatch means for measuring and displaying time elapsed from an operation of the time-measurement-start commanding/operating means, the stopwatch means stopping the time measurement if freeze-on is commanded.

In the ultrasonic diagnostic apparatus of the eleventh aspect, since the time elapsed from the start of time measurement that is arbitrarily initiated to the time at which a freeze-on operation was made is measured and displayed, how long has passed from the start of examination to the time the freeze screen was captured, for example, can be confirmed on the display screen.

In its twelfth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; time-measurement-start commanding/operating means for use by the operator to operate to command start of time measurement; countdown means for counting down from an initial value to zero starting with an operation of the time-measurement-start commanding/operating means; and initial value setting means for use by the operator to set the initial value.

In the ultrasonic diagnostic apparatus of the twelfth aspect, since the time remaining to the time at which a certain operation is to be made after start of time measurement that is arbitrarily initiated can be measured and displayed, the operator need not check a separately provided watch, and can concentrate on the display screen to move ahead with the certain protocol.

In its thirteenth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; freezing means for maintaining a state displaying the last ultrasonic image in response to a freeze-on command by an operator; time-measurement-start commanding/operating means for use by the operator to operate to command start of time measurement; elapsed-time measuring means, which is not stopped even if freeze-on is commanded, for measuring and displaying time elapsed from an operation of the time-measurement-start commanding/operating means; countdown means for counting down from an initial value to zero starting with an operation of the time-measurement-start commanding/operating means; initial value setting means for use by the operator to set the initial value; and selection operating means for allowing the operator to select and activate both or one of the elapsed-time measuring means and the countdown means.

In the ultrasonic diagnostic apparatus of the thirteenth aspect, since the time elapsed from the start of time measurement that is arbitrarily initiated and/or the time remaining to the time at which a certain first operation is to be made after start of time measurement that is arbitrarily initiated is measured and displayed during a run of an arbitrary protocol, the operator need not check a separately provided watch, and can concentrate on the display screen to move ahead with the arbitrary protocol.

In its fourteenth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; intermittent imaging control means for controlling the aforementioned means to produce an ultrasonic image at a frame rate less than one; and elapsed-time measuring means for measuring and displaying time elapsed from a time at which a currently displayed ultrasonic image was captured.

In the ultrasonic diagnostic apparatus of the fourteenth aspect, the time elapsed from the time at which the currently displayed ultrasonic image was captured can be confirmed on a display screen in intermittent imaging.

In its fifteenth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; intermittent imaging control means for controlling the aforementioned means to produce an ultrasonic image at a frame rate less than one; and wait-time measuring means for measuring and displaying wait time until a time at which a next ultrasonic image is to be captured.

In the ultrasonic diagnostic apparatus of the fifteenth aspect, the wait time until the ultrasonic image is to be next updated can be confirmed on the display screen in intermittent imaging.

In its sixteenth aspect, the present invention provides an ultrasonic diagnostic apparatus characterized in comprising: an ultrasonic probe; transmitting/receiving means for driving the ultrasonic probe to transmit an ultrasonic pulse into a subject and receiving an ultrasonic echo from the subject to output received data; ultrasonic image producing means for producing an ultrasonic image from the resulting received data; display means for displaying the produced ultrasonic image; intermittent imaging control means for controlling the aforementioned means to produce an ultrasonic image at a frame rate less than one; elapsed-time measuring means for measuring and displaying time elapsed from a time at which a currently displayed ultrasonic image was captured; wait-time measuring means for measuring and displaying wait time until a time at which a next ultrasonic image is to be captured; and selection operating means for allowing the operator to select and activate both or one of the elapsed-time measuring means and the wait-time measuring means.

In the ultrasonic diagnostic apparatus of the sixteenth aspect, the time elapsed from the time at which the currently displayed ultrasonic image was captured and/or the wait time until the ultrasonic image is to be next updated can be confirmed on the display screen in intermittent imaging.

According to the ultrasonic diagnostic apparatus of the present invention, time progress during a run of a contrast agent protocol, time progress during intermittent imaging and the like can be confirmed on a display screen. Therefore, the need to check a separately provided watch is eliminated, and the operator can concentrate on a display screen to move ahead with diagnosis. Thus, work efficiency is improved.

Further objects and advantages of the present invention will be apparent from the following description of the preferred embodiments of the invention as illustrated in the accompanying drawings.

DETAILED DESCRIPTION OF THE INVENTION

The present invention will now be described in more detail with reference to embodiments shown in the accompanying drawings.

Figure 1:
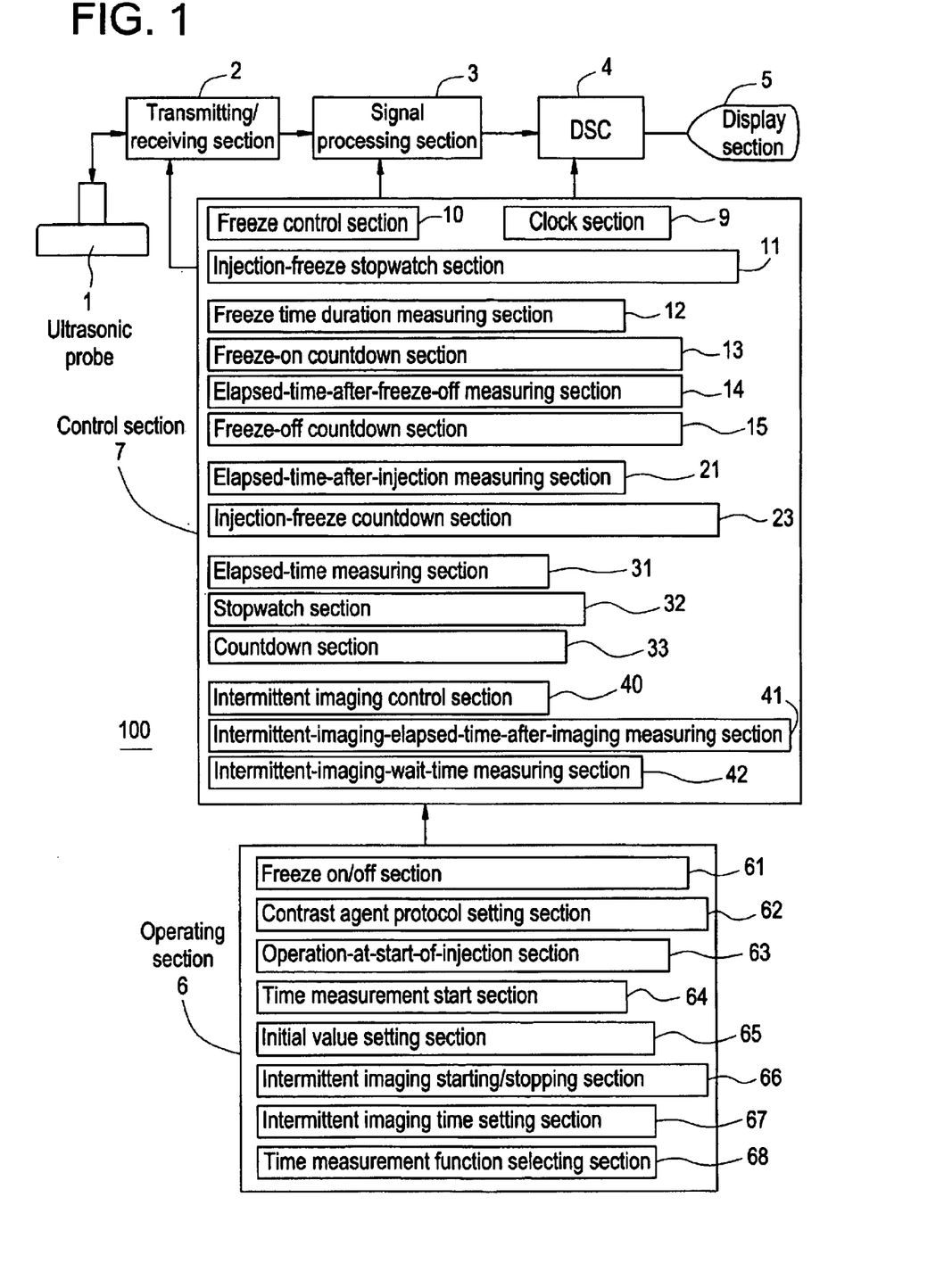
FIG. 1 is a configuration diagram showing an ultrasonic diagnostic apparatus in accordance with one embodiment of the present invention.

FIG. 1 is a configuration diagram of an ultrasonic diagnostic apparatus 100 in accordance with one embodiment of the present invention.

The ultrasonic diagnostic apparatus 100 comprises an ultrasonic probe 1, a transmitting/receiving section 2 for driving the ultrasonic probe 1 to transmit a transmission pulse in a desired acoustic line direction and receiving an ultrasonic echo in the desired acoustic line direction by the ultrasonic probe 1 to output an acoustic line signal, a signal processing section 3 for generating ultrasonic image data based on the received signal, a DSC (digital scan converter) 4 for generating display data from the ultrasonic image data and several kinds of timer information in accordance with the present invention, a display section 5 for displaying an ultrasonic image and timer information based on the display data, an operating section 6 for use by an operator to make an input operation, and a control section 7 for controlling the transmitting/receiving section 2, signal processing section 3 and DSC 4.

The operating section 6 comprises a freeze on/off section 61 for use by the operator to make a freeze-on operation and a freeze-off operation, a contrast agent protocol setting section 62 for setting a contrast agent protocol, an operation-at-start-of-injection section 63 for operation by the operator when a contrast agent is injected, a time measurement starting section 64 for operation by the operator when arbitrary time measurement is to be started, an initial value setting section 65 for setting a time period from the start of the arbitrary time measurement to a time at which a certain operation is to be made, an intermittent imaging starting/stopping section 66 for use by the operator to make a start/stop operation of intermittent imaging in which an ultrasonic image is produced at a frame rate less than one, an intermittent imaging time setting section 67 for setting an interval in the intermittent imaging, and a time measurement function selecting section 68 for use by the operator to select which of several time measurement functions to activate.

The control section 7 comprises a clock section 9 for keeping the current date and time and generating date/time information, a freeze control section 10 for maintaining a state displaying the last ultrasonic image in response to a freeze-on operation by the operator and resuming production/display of a new ultrasonic image in response to a freeze-off operation by the operator, an injection-freeze stopwatch section 11 for measuring time elapsed starting with zero upon operation of the operation-at-start-of-injection section 63 up to a time at which a freeze-on command operation is made, a freeze time duration measuring section 12 for measuring the time duration of the freeze state starting with zero upon the freeze-on operation, a freeze-on countdown section 13 for measuring time remaining from the current time to a time at which a next freeze-on operation is to be made, an elapsed-time-after-freeze-off measuring section 14 for measuring time elapsed starting with zero upon a freeze-off operation, and a freeze-off countdown section 15 for measuring time remaining from the current time to a time at which a next freeze-off operation is to be made.

Moreover, the control section 7 comprises an elapsed-time-after-injection measuring section 21 for measuring time elapsed starting with zero from an operation of the operation-at-start-of-injection section 63, an injection-freeze countdown section 23 for measuring time remaining from the current time to a time at which a first freeze-on operation is to be made after the operation of the operation-at-start-of-injection section 63, an elapsed-time measuring section 31 for measuring time elapsed starting with zero upon an operation of the time measurement starting section 64, a stopwatch section 32 for, starting with zero upon an operation of the time measurement starting section 64, measuring elapsed time, and stopping the time measurement upon a freeze-on command, and a countdown section 33 for starting countdown from an initial value upon an operation of the time measurement starting section 64.

Furthermore, the control section 7 comprises an intermittent imaging control section 40 for starting intermittent imaging in response to an intermittent imaging start operation by the operator and resuming production/display of a new ultrasonic image at a regular frame rate (e.g., 30) in response to an intermittent imaging stop operation by the operator, an intermittent-imaging-elapsed-time-after-imaging measuring section 41 for measuring time elapsed from the time at which the currently displayed ultrasonic image was captured, and an intermittent-imaging-wait-time measuring section 42 for measuring wait time until a time at which a next ultrasonic image is to be captured.

Figure 2:
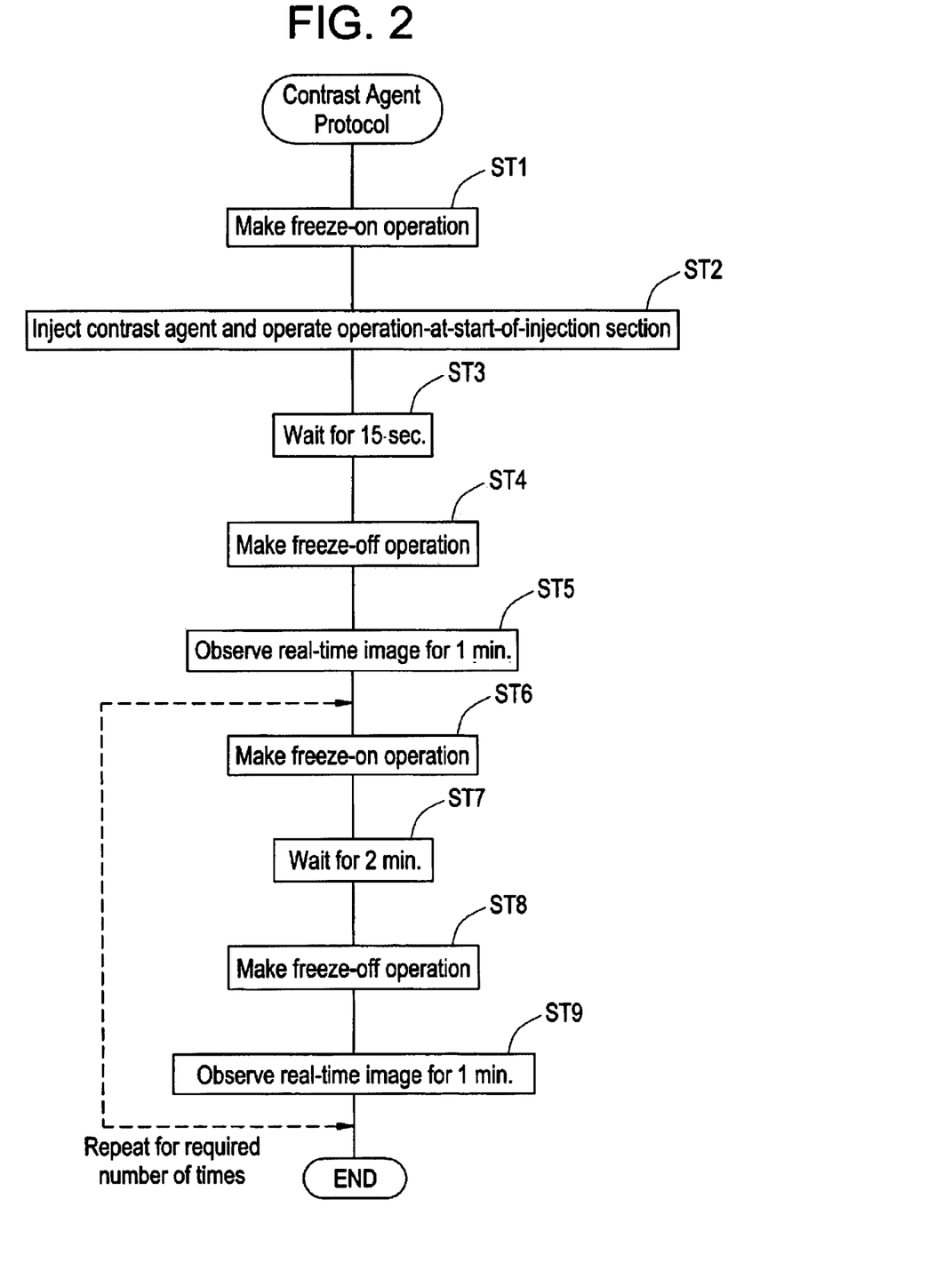
FIG. 2 is a flow chart showing an exemplary contrast agent protocol.

FIG. 2 is an explanatory diagram showing an exemplary contrast agent protocol set and stored by the contrast agent protocol setting section 62.

At Step ST1, a freeze-on operation is made.

At Step ST2, a contrast agent is injected into a subject. At the same time, the operation-at-start-of-injection section 63 is operated.

At Step ST3, fifteen seconds is allowed to pass for permeation of the contrast agent.

At Step ST4, a freeze-off operation is made.

At Step ST5, a real-time image is observed for one minute.

At Step ST6, a freeze-on operation is made.

At Step ST7, two minutes is allowed to pass for permeation of the contrast agent.

At Step ST8, a freeze-off operation is made.

At Step ST9, a real-time image is observed for one minute.

Steps ST6–ST9 are repeated for a required number of times, and the process is terminated.

Figure 3:
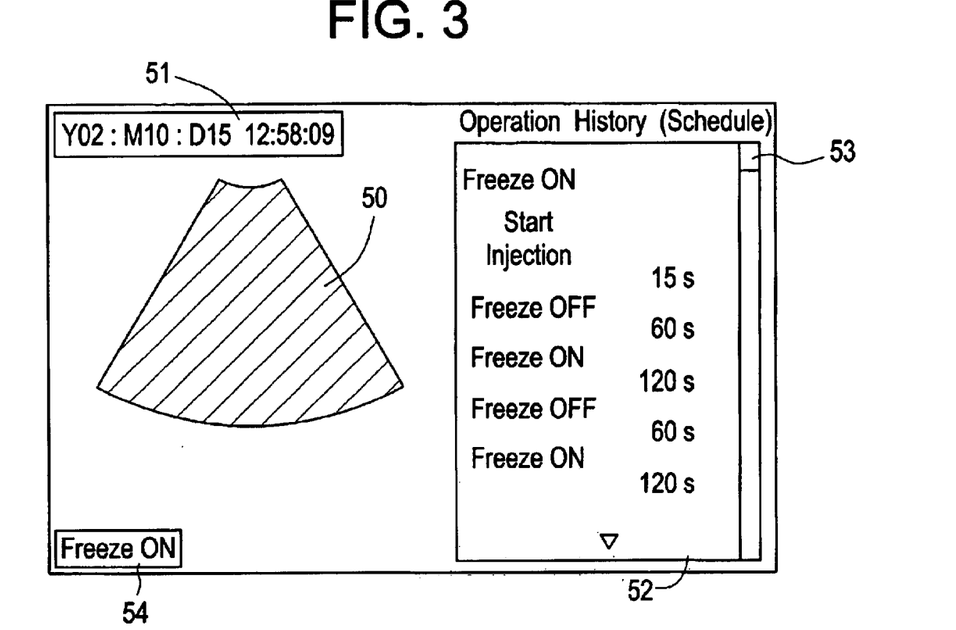
FIG. 3 is an exemplary diagram showing a display screen after invoking the contrast agent protocol shown in FIG. 2.

FIG. 3 is an exemplary diagram of a display screen when the operator makes an invoking operation at the contrast agent protocol setting section 62 and the stored contrast agent protocol of FIG. 2 is invoked.

In an ultrasonic image display region 50, a real-time image is presented.

In a date/time display region 51, the current date and time are displayed.

In a contrast protocol display region 52, the invoked contrast agent protocol is displayed. Time intervals are displayed between scheduled operations.

In a progress display region 53, progress of the contrast agent protocol is displayed.

In a next-operation display region 54, the next operation to be made by the operator, i.e., "Freeze ON," is displayed.

Figure 4:
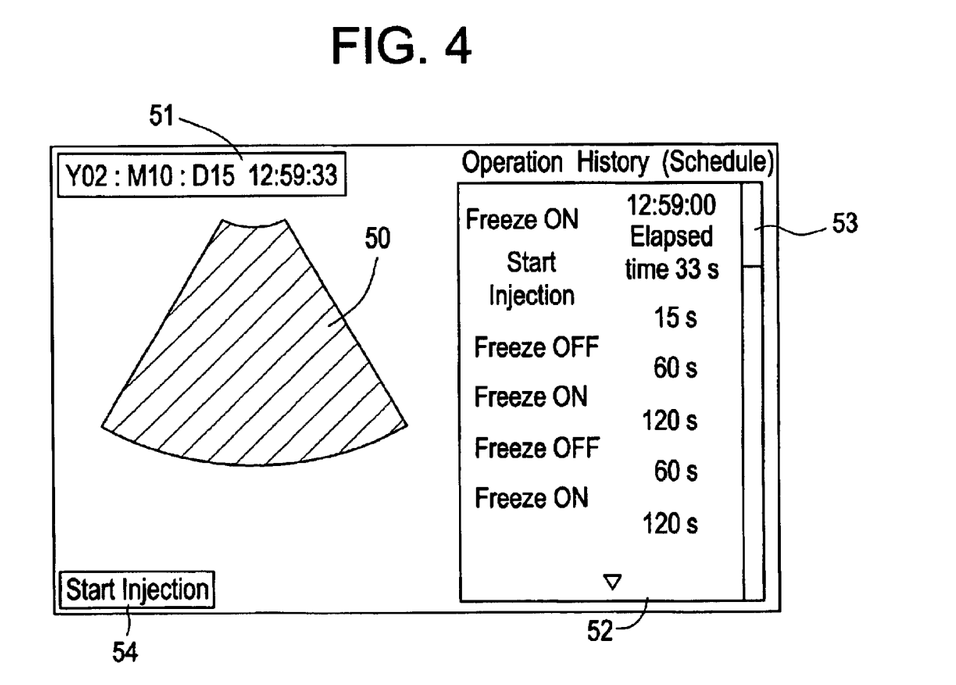
FIG. 4 is an exemplary diagram showing a display screen after freeze-on and before start of injection in the contrast agent protocol shown in FIG. 2.

FIG. 4 is an exemplary diagram of a display screen when the operator makes a freeze-on operation at the freeze on/off section 61 to bring about a freeze state before contrast agent injection in the contrast agent protocol.

In the ultrasonic image display region 50, a freeze image is presented.

In the date/time display region 51, the current date and time are displayed.

In the contrast protocol display region 52, the time of the freeze-on, i.e., "12:59:00," and the time elapsed thereafter, i.e., "33 s," are displayed as a history.

In the next-operation display region 54, the next operation to be made by the operator, i.e., "Start Injection," is displayed.

Figure 5:
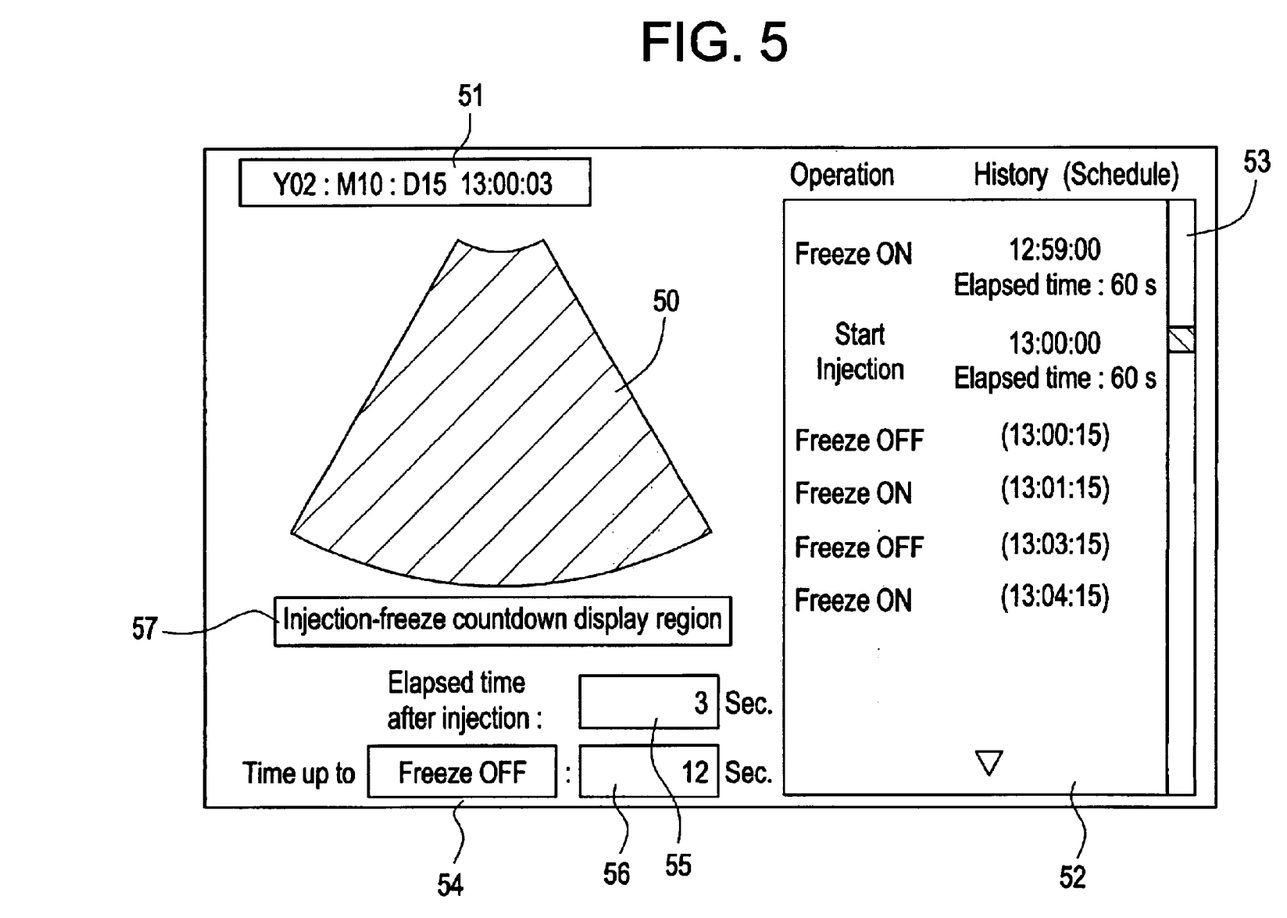
FIG. 5 is an exemplary diagram showing a display screen after contrast agent injection and before freeze-off in the contrast agent protocol shown in FIG. 2.

FIG. 5 is an exemplary diagram of a display screen just after the operator has injected the contrast agent into the subject and at the same time operated the operation-at-start-of-injection section 63.

In the ultrasonic image display region 50, a freeze image is presented.

In the contrast agent protocol display region 52, the time of the operation of the operation-at-start-of-injection section 63, i.e., "13:00:00," and the time elapsed thereafter, i.e., "3 s," are displayed as a history. The elapsed time of the freeze state before the contrast agent injection, "60 s," is stopped at the time elapsed up to the operation of the operation-at-start-of-injection section 63. Moreover, scheduled times of the scheduled operations are calculated and displayed.

In the progress display region 53, progress of the contrast agent protocol after the operation of the operation-at-start-of-injection section 63 is displayed.

In an elapsed-time-after-injection display region 55, the elapsed time from the operation of the operation-at-start-of-injection section 63 is displayed.

In a countdown display region 56, the time remaining up to the scheduled time of the next operation to be made by the operator is calculated and displayed.

In an injection-freeze countdown display region 57, the time remaining up to the scheduled time at which a first freeze-on operation is to be made after operation of the operation-at-start-of-injection section 63 is calculated and displayed. This display appears only in the period from start of injection to the first freeze-on command.

Figure 6:
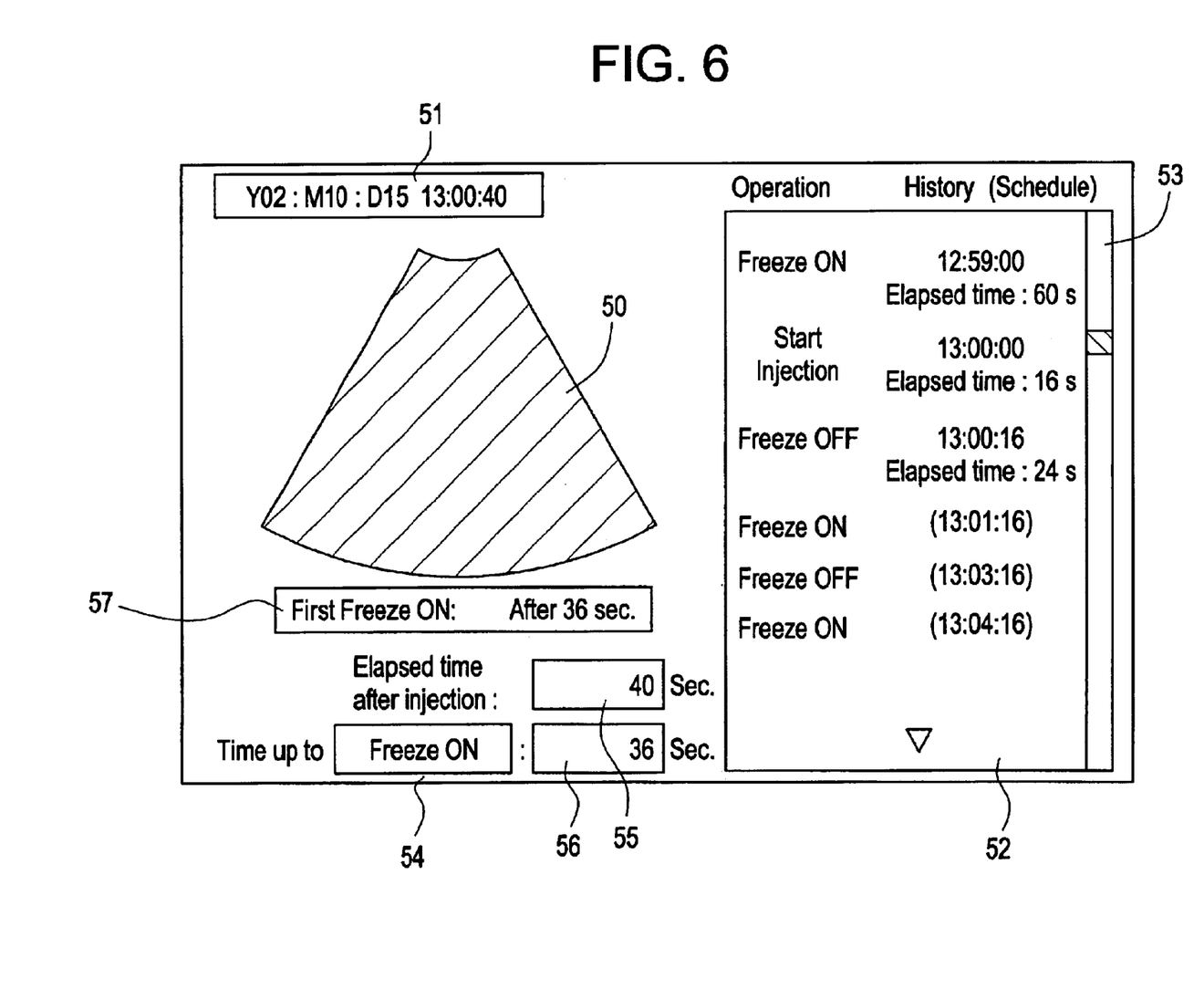
FIG. 6 is an exemplary diagram showing a display screen after contrast agent injection and before first freeze-on in the contrast agent protocol shown in FIG. 2.

FIG. 6 is an exemplary diagram of a display screen after the operator has operated the freeze on/off section 61 to turn off freeze after injecting the contrast agent into the subject.

In the ultrasonic image display region 50, a real-time image is presented.

In the contrast agent protocol display region 52, the time of the freeze-off, i.e., "13:00:16," and the time elapsed thereafter, i.e., "24 s," are displayed as a history. The time elapsed after the freeze-off after the contrast agent injection, i.e., "16 s," is stopped at the time elapsed up to the freeze-off. Moreover, the scheduled times of scheduled operations are calculated and displayed.

Figure 7:
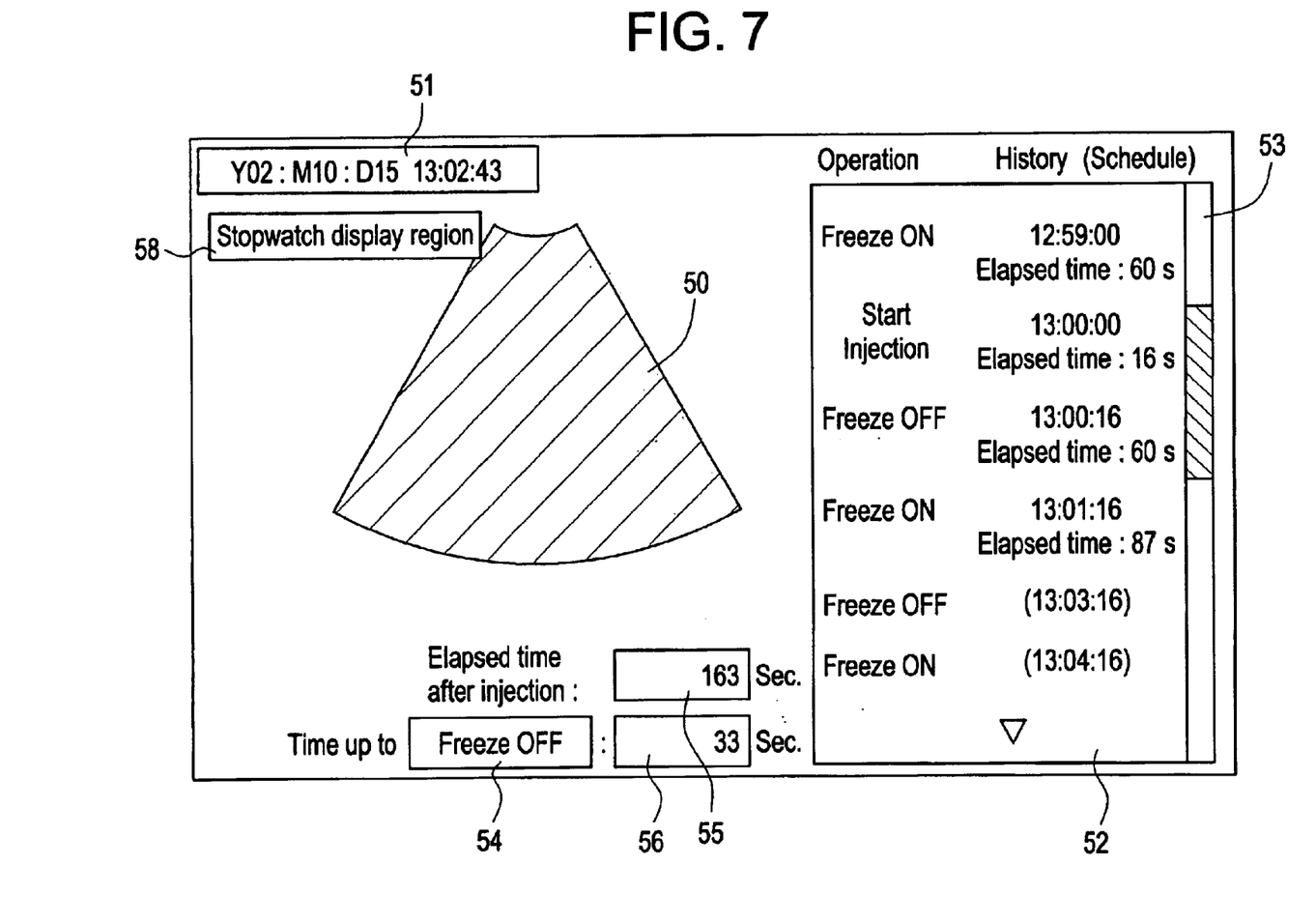
FIG. 7 is an exemplary diagram showing a display screen after the first freeze-on in the contrast agent protocol shown in FIG. 2.

FIG. 7 is an exemplary diagram of a display screen after the operator has operated the freeze on/off section 61 to first turn on freeze after injecting the contrast agent into the subject.

In the ultrasonic image display region 50, a freeze image is presented.

In the contrast agent protocol display region 52, the time of the freeze-on, i.e., "13:01:16," and the time duration thereafter, i.e., "87 s," are displayed as a history. The time elapsed after the freeze-off, i.e., "60 s," is stopped at the time elapsed up to the freeze-on.

In a stopwatch display region 58, the time elapsed from the time of the operation of the operation-at-start-of-injection section 63 to the time of the freeze-on operation is displayed. This display appears only along with a freeze image produced by turning on freeze after start of injection.

The operator may operate the time measurement function selecting section 68 to clear one or both of the countdown display region 56, and the elapsed time after freeze-off and time duration of freeze in FIGS. 5–7.

Figure 8:
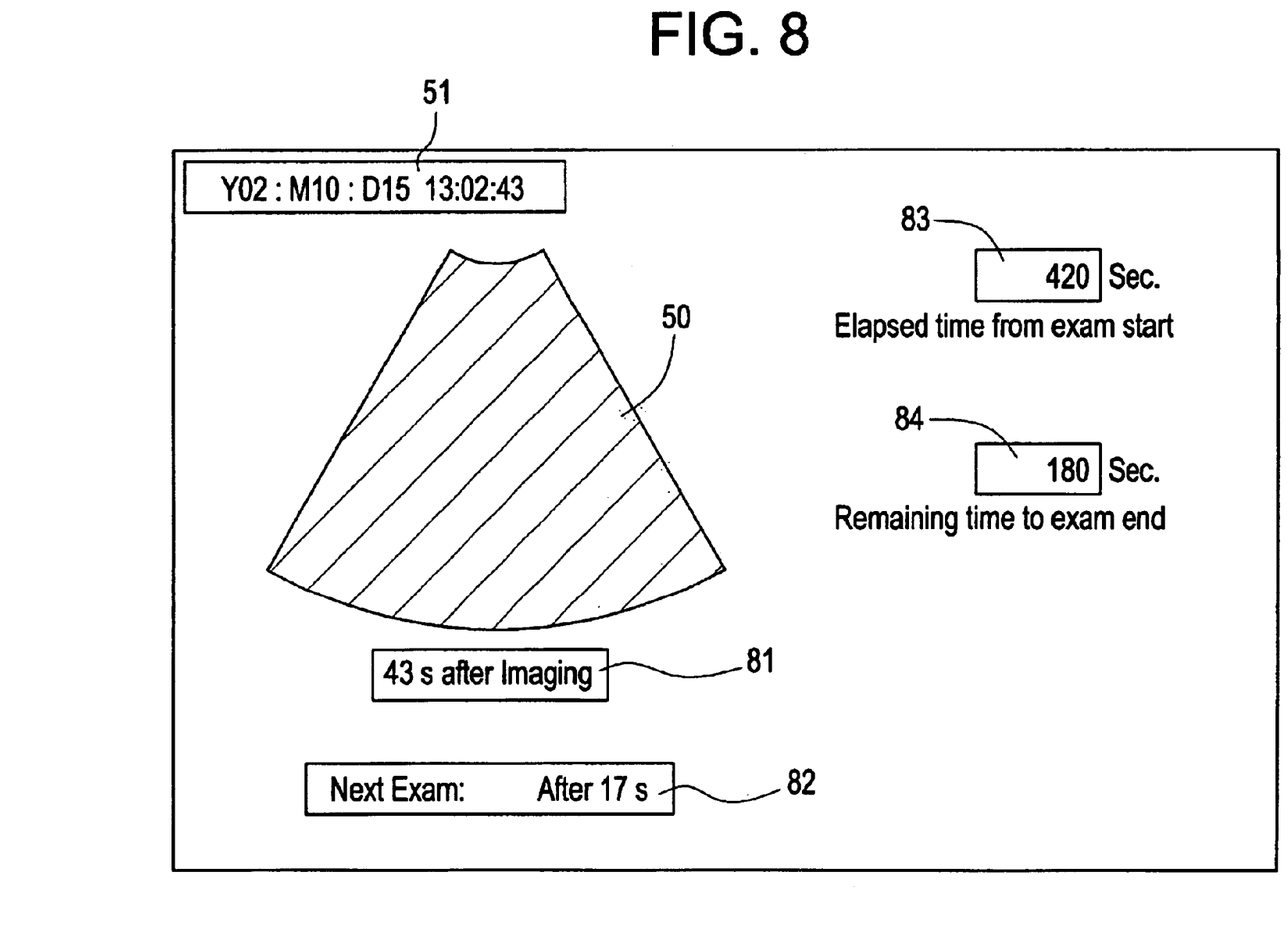
FIG. 8 is an exemplary diagram showing a display screen during an examination by intermittent imaging.

FIG. 8 is an exemplary diagram of a display screen during an examination by intermittent imaging.

The operator sets a required examination time (e.g., ten minutes) at the initial value setting section 65 before start of examination, and operates the time measurement start section 64 at the start of examination.

In the ultrasonic image display region 50, a freeze image is presented. The freeze image is updated at a frame rate less than one (e.g., 1/60).

In an elapsed time display region 81, the time elapsed from the capture of the displayed freeze image is displayed.

In a wait time display region 82, the wait time until the displayed freeze image is to be updated is displayed.

In an examination elapsed time display region 83, the time elapsed from the operation of the time measurement start section 64 is displayed.

In an examination countdown display region 84, the time obtained by subtracting the elapsed time from the operation of the time measurement start section 64 from the required examination time set at the initial value setting section 61 is calculated and displayed.

The operator may operate the time measurement function selecting section 68 to clear one or both of the elapsed time display region 81 and the wait time display region 82 in FIG. 8. Moreover, the operator may clear one or both of the examination elapsed time display region 83 and the examination countdown display region 84.

Other Embodiments (1) For example, the next-operation display region 54 and countdown display region 56 may be displayed with blinking, with highlighting or in color to alert the operator.

(2) The display regions may be configured so that their positions can be moved and shapes changed by operation of a mouse, for example.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus comprising:

an ultrasonic probe;

a transmitting/receiving device for driving the ultrasonic probe to transmit an ultrasonic pulse into a subject and receiving an ultrasonic echo from the subject to output received data;

an ultrasonic image producing device for producing an ultrasonic image from the resulting received data;

a display device for displaying the produced ultrasonic image;

a freeze control device for maintaining a state displaying the last ultrasonic image in response to a freeze-on operation by an operator and resuming production/display of a new ultrasonic image in response to a freeze-off operation by the operator; and a freeze time duration measuring device for measuring and displaying time duration of the freeze state.

2. An ultrasonic diagnostic apparatus comprising:

an ultrasonic probe;

a transmitting/receiving device for driving the ultrasonic probe to transmit an ultrasonic pulse into a subject and receiving an ultrasonic echo from the subject to output received data;

an ultrasonic image producing device for producing an ultrasonic image from the resulting received data;

a display device for displaying the produced ultrasonic image;

a freeze control device for maintaining a state displaying the last ultrasonic image in response to a freeze-on operation by an operator and resuming production/display of a new ultrasonic image in response to a freeze-off operation by the operator; and an elapsed-time-from-freeze-off measuring device for measuring and displaying an elapsed time from freeze-off.

3. An ultrasonic diagnostic apparatus comprising:

an ultrasonic probe;

a transmitting/receiving device for driving the ultrasonic probe to transmit an ultrasonic pulse into a subject and receiving an ultrasonic echo from the subject to output received data;

an ultrasonic image producing device for producing an ultrasonic image from the resulting received data;

a display device for displaying the produced ultrasonic image;

a freezing device for maintaining a state displaying the last ultrasonic image in response to a freeze-on command by an operator;

an operation-at-start-of-injection device for operation by the operator at the start of contrast agent injection; and an elapsed-time-from-injection measuring device, which is not stopped even if freeze-on is commanded, for measuring and displaying time elapsed from an operation of the operation-at-start-of-injection device.

4. An ultrasonic diagnostic apparatus comprising:

an ultrasonic probe;

a transmitting/receiving device for driving the ultrasonic probe to transmit an ultrasonic pulse into a subject and receiving an ultrasonic echo from the subject to output received data;

an ultrasonic image producing device for producing an ultrasonic image from the resulting received data;

a display device for displaying the produced ultrasonic image;

a freezing device for maintaining a state displaying the last ultrasonic image in response to a freeze-on command by an operator;

a time-measurement-start commanding/operating device for use by the operator to operate to command start of time measurement; and an elapsed-time measuring device, which is not stopped even if freeze-on is commanded, for measuring and displaying time elapsed from an operation of the time-measurement-start commanding/operating device.

5. An ultrasonic diagnostic apparatus comprising:

an ultrasonic probe;

a transmitting/receiving device for driving the ultrasonic probe to transmit an ultrasonic pulse into a subject and receiving an ultrasonic echo from the subject to output received data;

an ultrasonic image producing device for producing an ultrasonic image from the resulting received data;

a display device for displaying the produced ultrasonic image;

an intermittent imaging control device for controlling the aforementioned device to produce an ultrasonic image at a frame rate less than one; and an elapsed-time measuring device for measuring and displaying time elapsed from a time at which a currently displayed ultrasonic image was captured.

* * * * *